(12) United States Patent
Ota et al.

(10) Patent No.: US 11,373,348 B2
(45) Date of Patent: Jun. 28, 2022

(54) DISPLAY DEVICE

(71) Applicant: SINTOKOGIO, LTD., Nagoya (JP)

(72) Inventors: Kazuhiro Ota, Toyokawa (JP); Yuichi Ogura, Toyokawa (JP); Takeshi Sonohara, Toyokawa (JP)

(73) Assignee: SINTOKOGIO, LTD., Aichi (JP)

( * ) Notice: Subject to any disclaimer, the term of this patent is extended or adjusted under 35 U.S.C. 154(b) by 0 days.

(21) Appl. No.: 17/057,177

(22) PCT Filed: Mar. 13, 2020

(86) PCT No.: PCT/JP2020/011003
§ 371 (c)(1),
(2) Date: Nov. 20, 2020

(87) PCT Pub. No.: WO2020/195922
PCT Pub. Date: Oct. 1, 2020

(65) Prior Publication Data
US 2021/0192811 A1    Jun. 24, 2021

(30) Foreign Application Priority Data
Mar. 28, 2019 (JP) .............................. JP2019-064759

(51) Int. Cl.
*G06T 11/00* (2006.01)
*G06T 11/20* (2006.01)
(Continued)

(52) U.S. Cl.
CPC .............. *G06T 11/206* (2013.01); *G01N 3/08* (2013.01); *G01N 15/08* (2013.01); *G01N 33/246* (2013.01); *G06F 3/14* (2013.01); *G06F 16/26* (2019.01)

(58) Field of Classification Search
CPC ......... G06T 11/206; G06F 16/26; G01N 3/08; G01N 15/08; G01N 33/246
See application file for complete search history.

(56) References Cited

U.S. PATENT DOCUMENTS

2015/0262396 A1\* 9/2015 Devarajan ............. G06F 3/0486
345/440.1

FOREIGN PATENT DOCUMENTS

| JP | 60-234737 A | 11/1985 |
|----|-------------|---------|
| JP | 2003-39135 A | 2/2003 |

(Continued)

OTHER PUBLICATIONS

"Molding sand 4.0, Molding sand Preparation in the age of Industry 4.0 or to make fruitful use of "Big Data" by the user", monthly journal "Journal of Foundry" issued by Japan Foundry Society, Inc, on Nov. 20, 2017.

(Continued)

*Primary Examiner* — Sarah Lhymn
(74) *Attorney, Agent, or Firm* — Harness, Dickey & Pierce, P.L.C.

(57) ABSTRACT

Provided is a display apparatus that is capable of displaying a relationship between sand properties measured as time series. The display apparatus displays (i) a relationship between pieces of measured first sand property data and pieces of measured second sand property data, obtained in a first predetermined period, together with first and second reference ranges set for the first and second sand properties and (ii) a relationship between pieces of measured third sand property data and pieces of measured fourth sand property data, obtained in a second predetermined period, together with third and fourth reference ranges set for the third and fourth sand properties.

6 Claims, 10 Drawing Sheets

(51) Int. Cl.
  *G06F 16/26* (2019.01)
  *G01N 3/08* (2006.01)
  *G01N 15/08* (2006.01)
  *G01N 33/24* (2006.01)
  *G06F 3/14* (2006.01)

(56) References Cited

FOREIGN PATENT DOCUMENTS

| | | |
|---|---|---|
| JP | 3480713 B2 | 12/2003 |
| JP | 2011-115848 A | 6/2011 |
| WO | WO-2014132269 A2 * | 9/2014 ............. B22C 19/04 |
| WO | WO-2018/101061 A1 | 6/2018 |

OTHER PUBLICATIONS

International Search Report PCT/ISA/210 for International Application No. PCT/JP2020/011003 dated Jun. 9, 2020.
International Report on Patentability dated Oct. 7, 2021.

* cited by examiner

FIG. 2
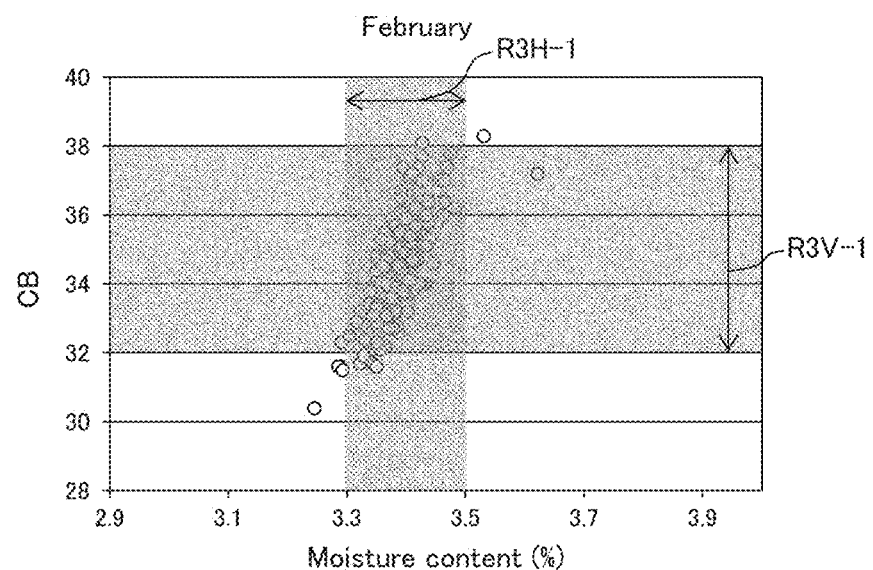
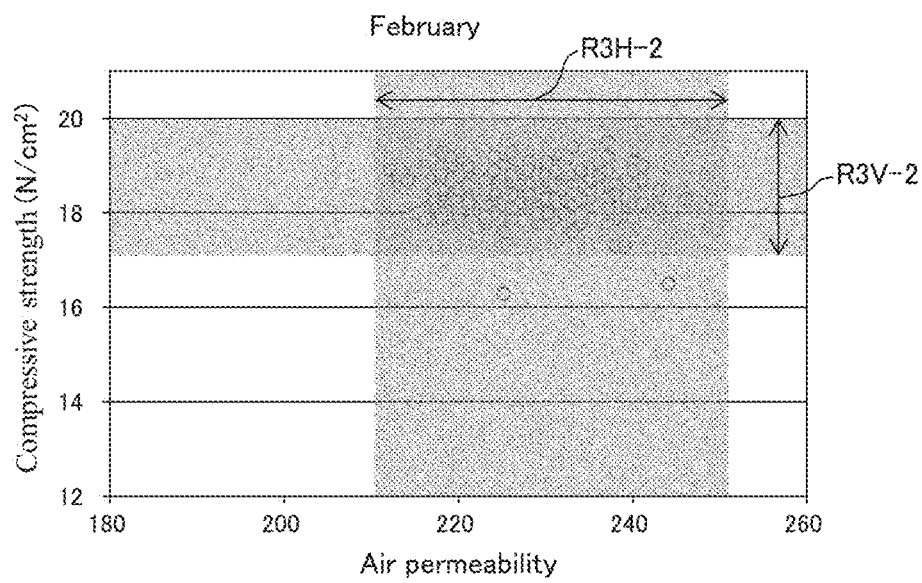

DISPLAY DEVICE

TECHNICAL FIELD

The present invention relates to a display apparatus.

BACKGROUND ART

Patent Literature 1 discloses an apparatus to predict changes in effective clay content/particle size distribution of foundry sand. This change prediction apparatus finds and predicts changes in effective clay content/particle size distribution of foundry sand before casting defects occur. According to the change prediction apparatus of Patent Literature 1, a sand characteristics measuring device measures compressive strength and/or air permeability, measured data is displayed, and, on the basis of the result of comparison between the measured data and predetermined design values, unusual changes in effective clay content/particle size distribution are predicted. In a case where an unusual change is predicted, a prepared remedial measure is proposed (claims 1 and 2, paragraphs 0012, 0016, 0018-0022, and FIG. 1 of Patent Literature 1).

Non-patent Literature 1 discloses a diagram showing a relationship between (i) the upper and lower limits of moisture content of foundry sand and (ii) the upper and lower limits of compactability (CB) of the foundry sand, and a relationship, calculated from the above-mentioned relationship, between (a) the upper and lower limits of the correlation coefficient between moisture and CB and (b) the upper and lower limits of compressive strength (FIG. 7 of Non-patent Literature 1).

CITATION LIST

Patent Literature

[Patent Literature 1]
Japanese Patent Application Publication Tokukai No. 2003-39135

Non-Patent Literature

[Non-Patent Literature 1]
"Molding sand 4.0, Molding sand Preparation in the age of Industry 4.0 or to make fruitful use of "Big Data" by the user", monthly journal "Journal of Foundry" issued by Japan Foundry Society, Inc. on Nov. 20, 2017

SUMMARY OF INVENTION

Technical Problem

The conventional technique disclosed in Patent Literature 1, however, is a technique which uses the measured data obtained by measuring compressive strength and/or the measured data obtained by measuring air permeability independently of each other, and does not use pieces of measured data obtained by measuring different sand properties (such as CB, moisture content, sand temperature, air permeability, compressive strength) in combination. Therefore, in a case where a remedial measure is taken on the basis of prediction that has been made using only measured data obtained by measuring a certain sand property, it is necessary to check whether or not other sand properties are affected.

The conventional technique disclosed in Non-patent Literature 1 is a technique which uses pieces of measured data obtained by measuring different sand properties in combination; however, this is not a technique which uses a plurality of pieces of measured data obtained as a time series. Therefore, in a case where a remedial measure is taken on the basis of prediction that has been made using measured data obtained at a certain point in time, it is necessary to check how sand properties will change over time after the remedial measure is taken.

An object of an aspect of the present invention is to provide a display apparatus that is capable of displaying a relationship between sand properties measured as time series.

Solution to Problem

In order to attain the above object, a display apparatus in accordance with an aspect of the present invention is a display apparatus configured to display sand properties of foundry sand, including: a first graph display data preparing section configured to (i) acquire, from a storage device which stores therein pieces of measured data obtained by measuring each of sand properties as a time series and dates and times at which the respective pieces of measured data were obtained, pieces of measured first sand property data which were obtained in a first predetermined period and pieces of measured second sand property data which were obtained in the first predetermined period, and (ii) prepare first graph display data for use in displaying a first graph together with a first reference range and a second reference range, the first graph showing a relationship between the pieces of measured first sand property data and the pieces of measured second sand property data, the first reference range having been set for a first sand property, the second reference range having been set for a second sand property; a second graph display data preparing section configured to (a) acquire, from the storage device, pieces of measured third sand property data which were obtained in a second predetermined period and pieces of measured fourth sand property data which were obtained in the second predetermined period, and (b) prepare second graph display data for use in displaying a second graph together with a third reference range and a fourth reference range, the second graph showing a relationship between the pieces of measured third sand property data and the pieces of measured fourth sand property data, the third reference range having been set for a third sand property, the fourth reference range having been set for a fourth sand property; and a display section which includes a display area and which is configured to display the first graph and the second graph in the display area on the basis of the first graph display data and the second graph display data.

Advantageous Effects of Invention

An aspect of the present invention makes it possible to display a relationship between sand properties measured as time series.

(a) of FIG. 2 is a graph showing a relationship between measured moisture content data and measured CB data. (b) of FIG. 2 is a graph showing a relationship between measured air permeability data and measured compressive strength data.

Figure 3:
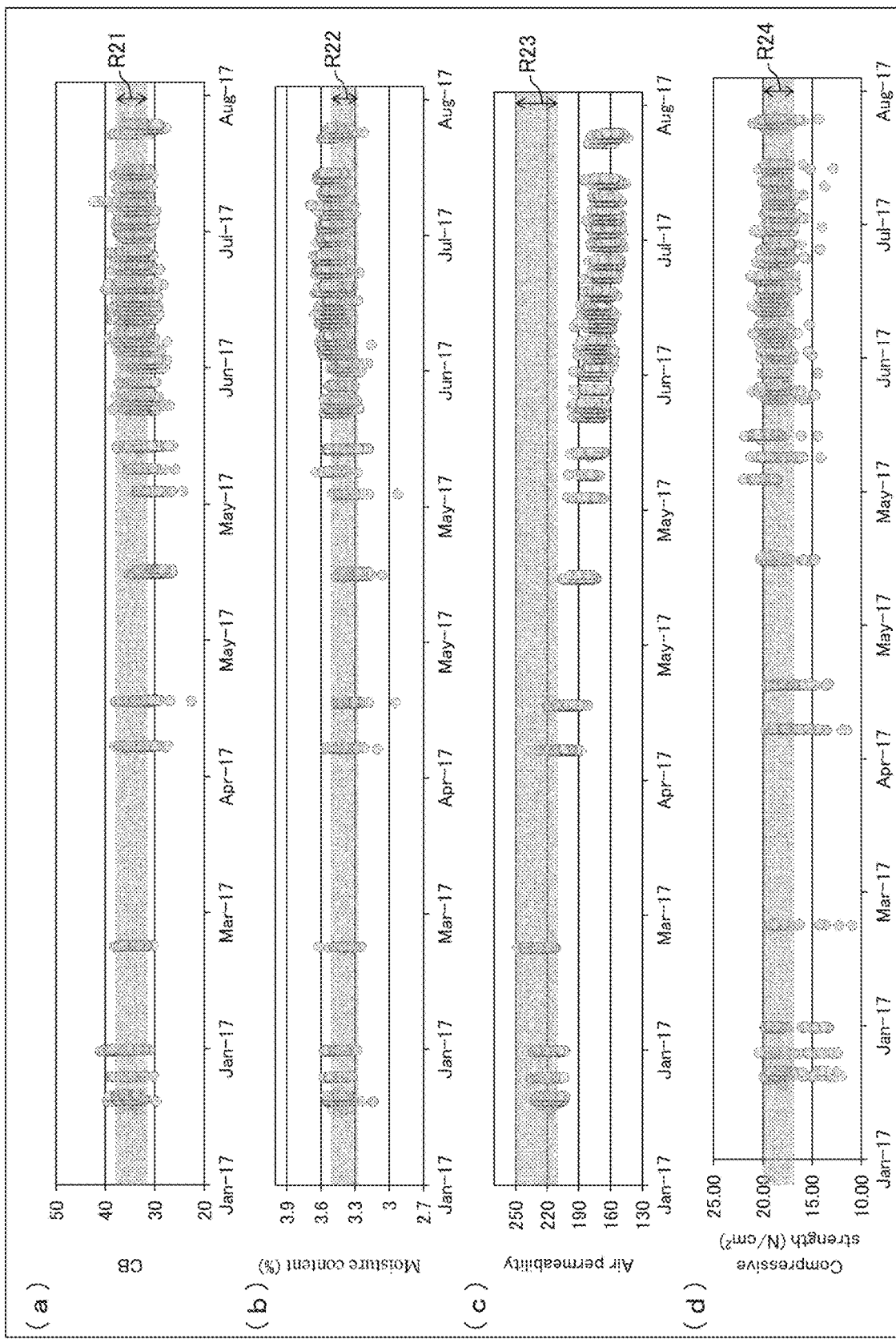

(a) of FIG. 3 is a graph showing measured CB data. (b) of FIG. 3 is a graph showing measured moisture content data. (c) of FIG. 3 is a graph showing measured air permeability data. (d) of FIG. 3 is a graph showing measured compressive strength data.

Figure 4:
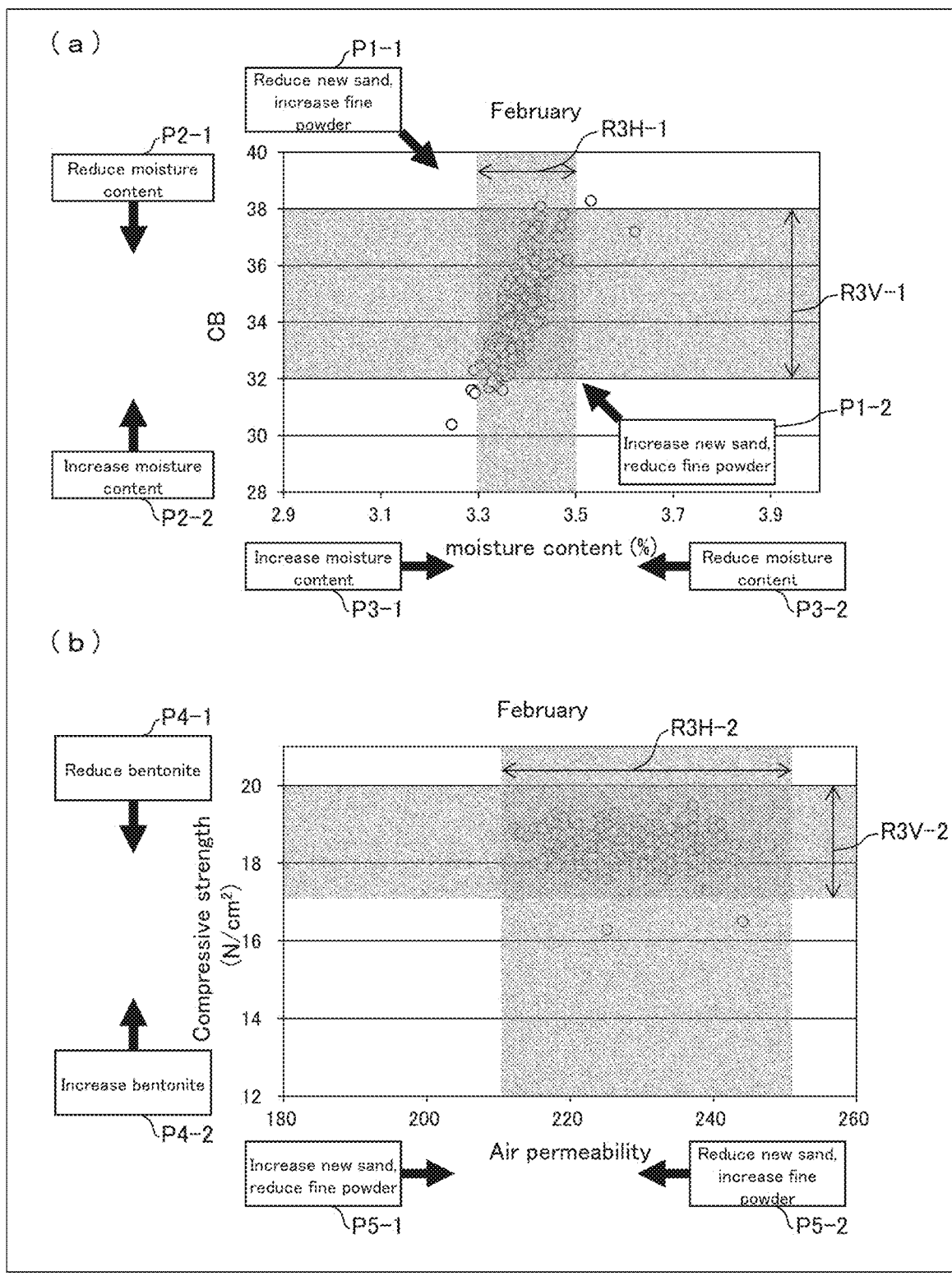

(a) of FIG. 4 is a graph showing a relationship between measured moisture content data and measured CB data. (b) of FIG. 4 is a graph showing a relationship between measured air permeability data and measured compressive strength data.

Figure 5:
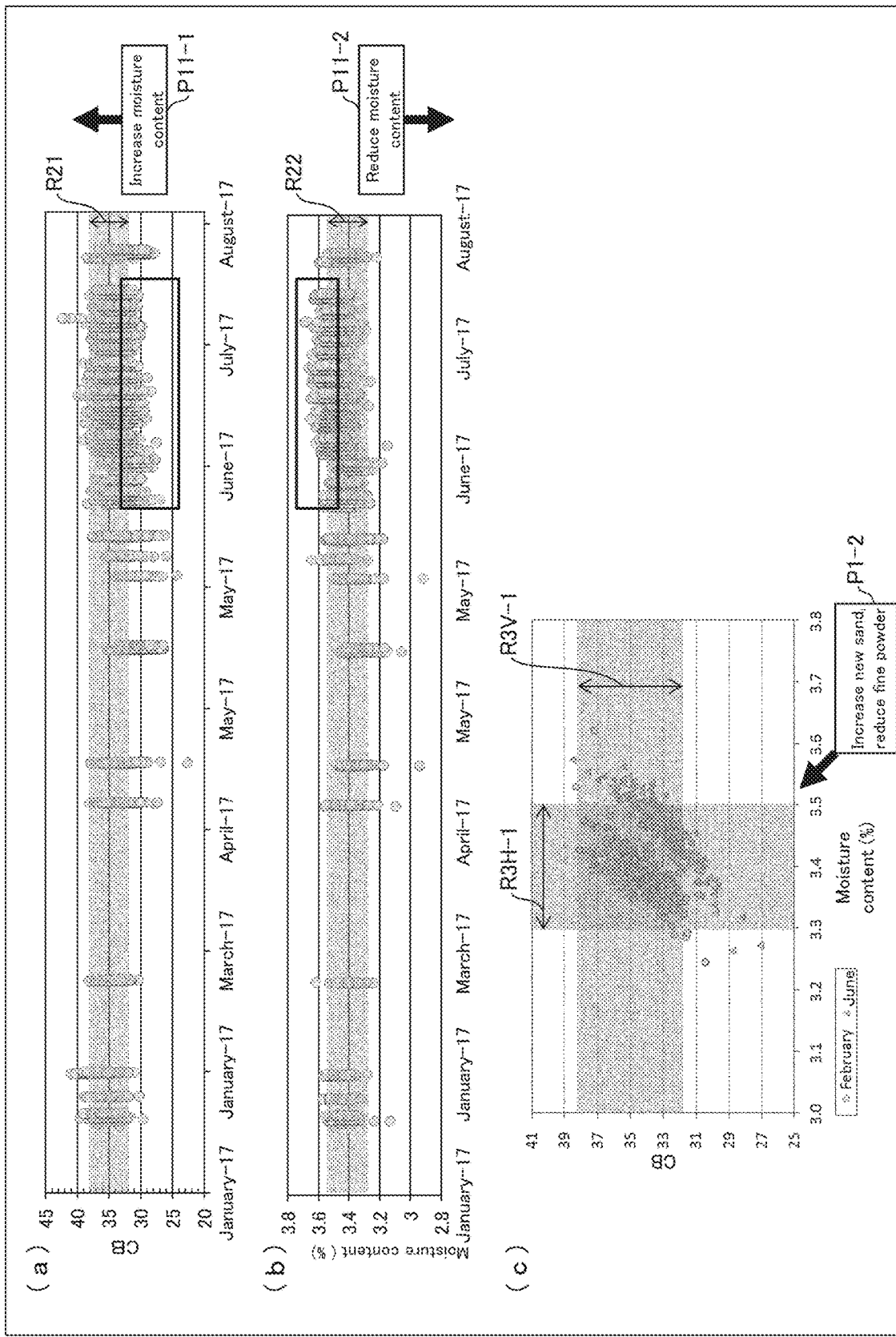

(a) of FIG. 5 is a graph showing measured CB data. (b) of FIG. 5 is a graph showing measured moisture content data. (c) of FIG. 5 is a graph showing a relationship between measured moisture content data and measured CB data.

Figure 6:
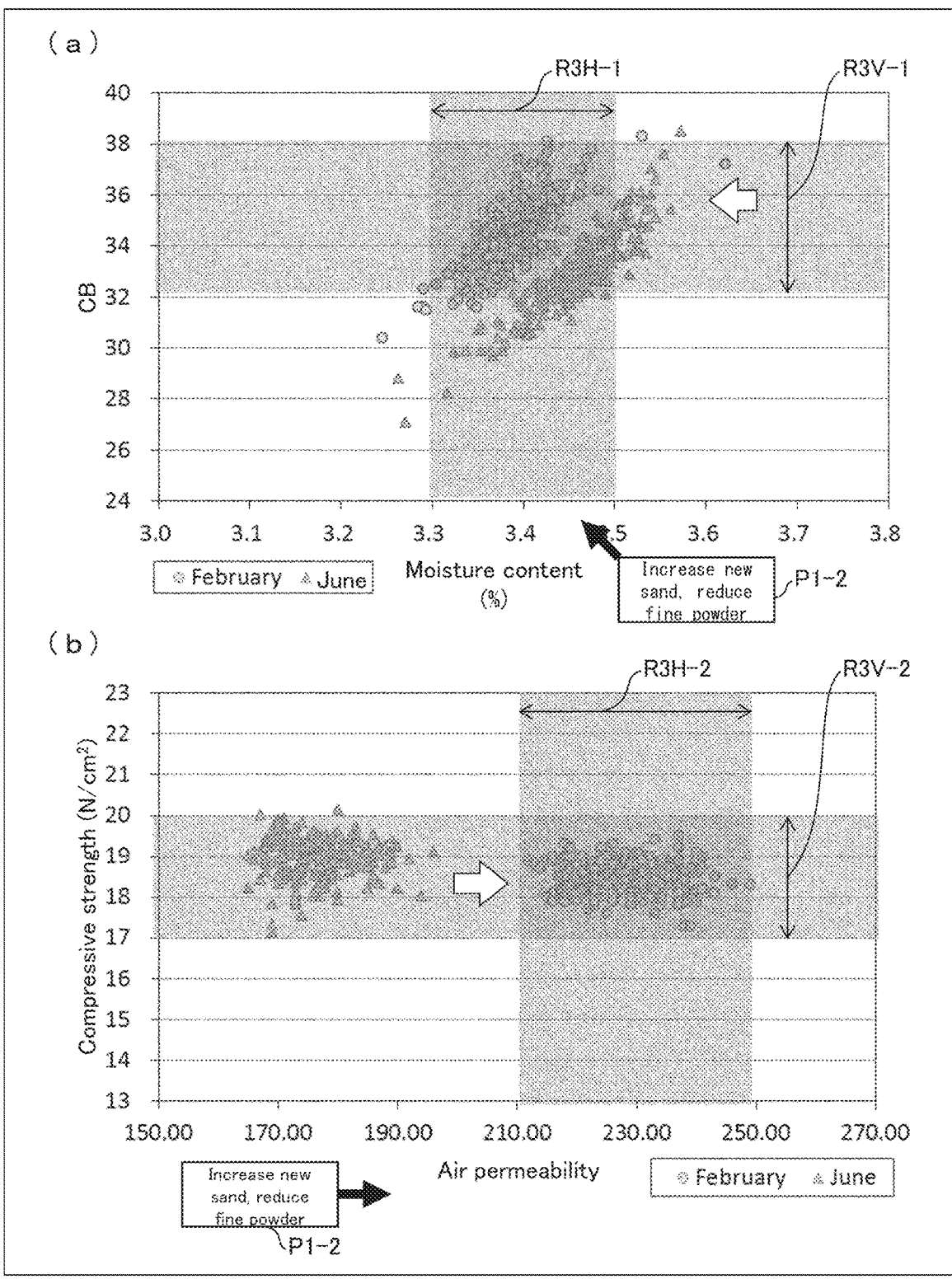

(a) of FIG. 6 is a graph showing a relationship between measured moisture content data and measured CB data. (b) of FIG. 6 is a graph showing a relationship between measured air permeability data and measured compressive strength data.

Figure 7:
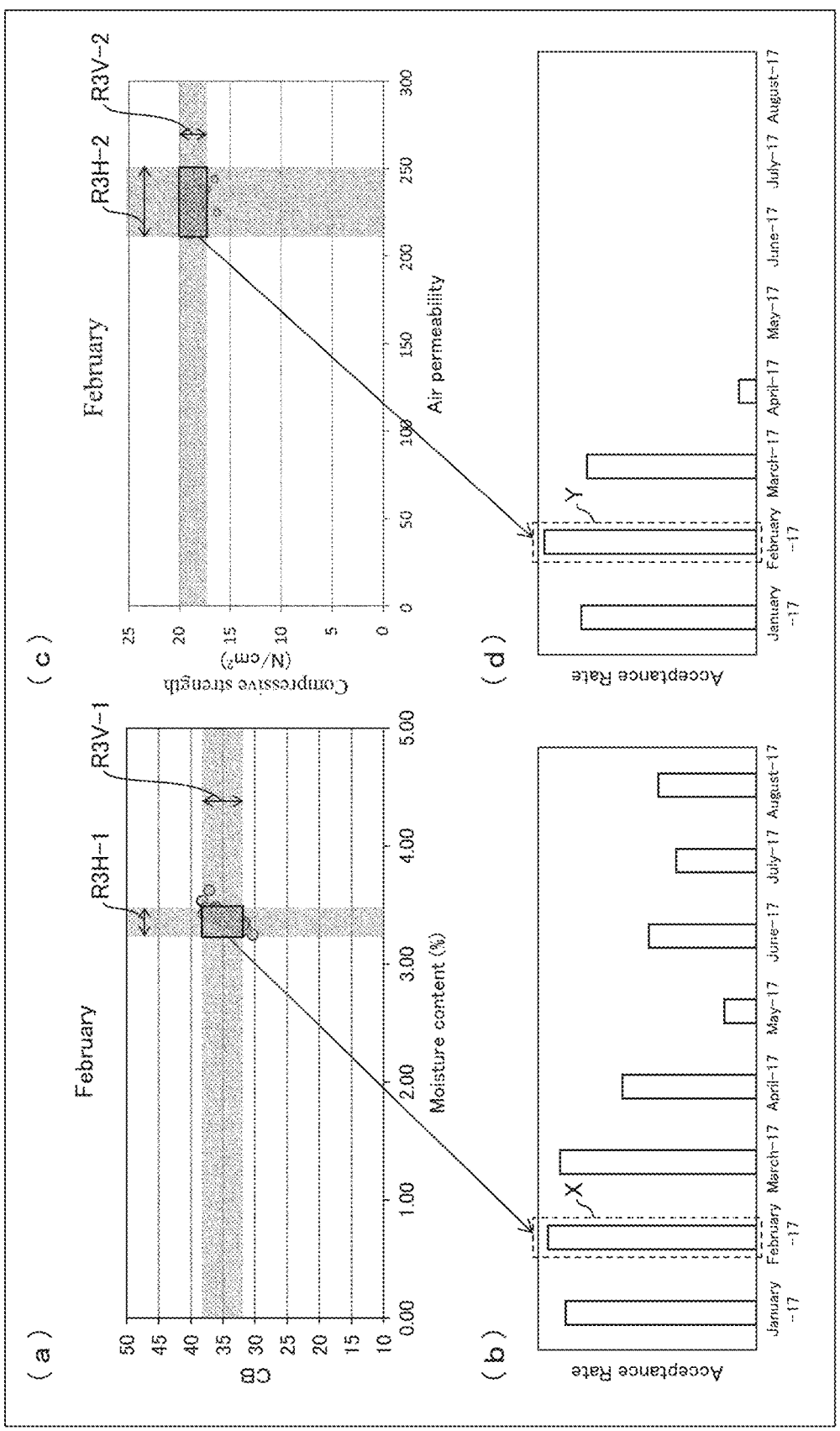

(a) of FIG. 7 is a graph showing a relationship between measured moisture content data and measured CB data. (b) of FIG. 7 is a graph showing acceptable rate which is the probability that a value of measured moisture content data and a value of measured CB data are both within respective predetermined reference ranges. (c) of FIG. 7 is a graph showing a relationship between measured air permeability data and measured compressive strength data. (d) of FIG. 7 is a graph showing acceptable rate which is the probability that a value of measured air permeability data and a value of measured compressive strength data are both within respective predetermined reference ranges.

Figure 8:
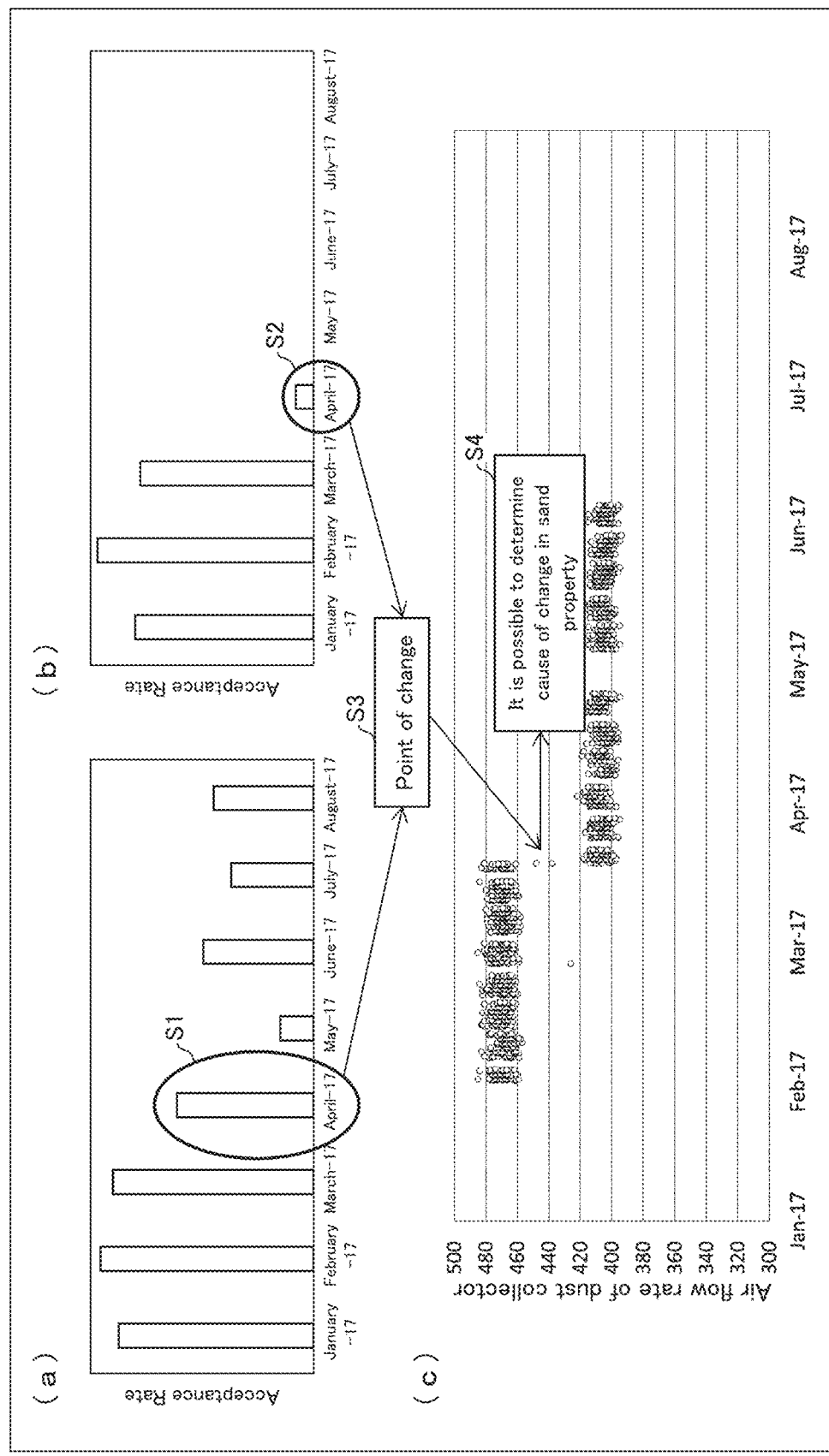

(a) of FIG. 8 is a graph showing acceptable rate which is the probability that a value of measured moisture content data and a value of measured CB data are both within respective predetermined reference ranges. (b) of FIG. 8 is a graph showing acceptable rate which is the probability that a value of measured air permeability data and a value of measured compressive strength data are both within respective predetermined reference ranges. (c) of FIG. 8 is a graph showing measured data obtained by measuring air flow rate of a dust collector.

Figure 9:
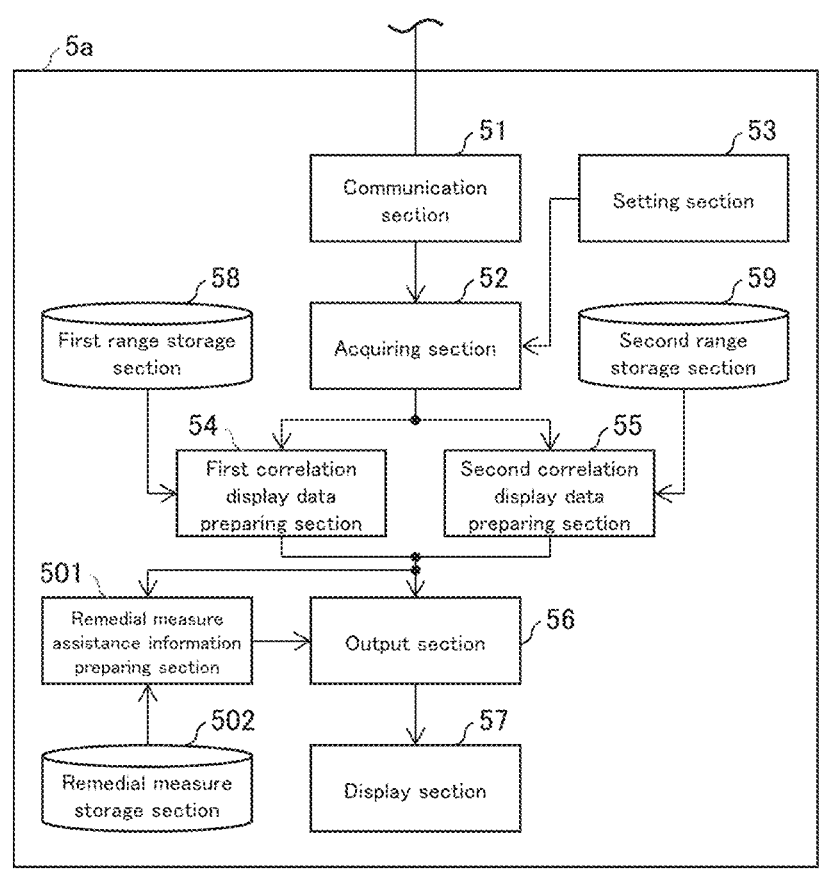

FIG. 9 is a block diagram illustrating a schematic configuration of a display apparatus in accordance with another embodiment of the present invention.

Figure 10:
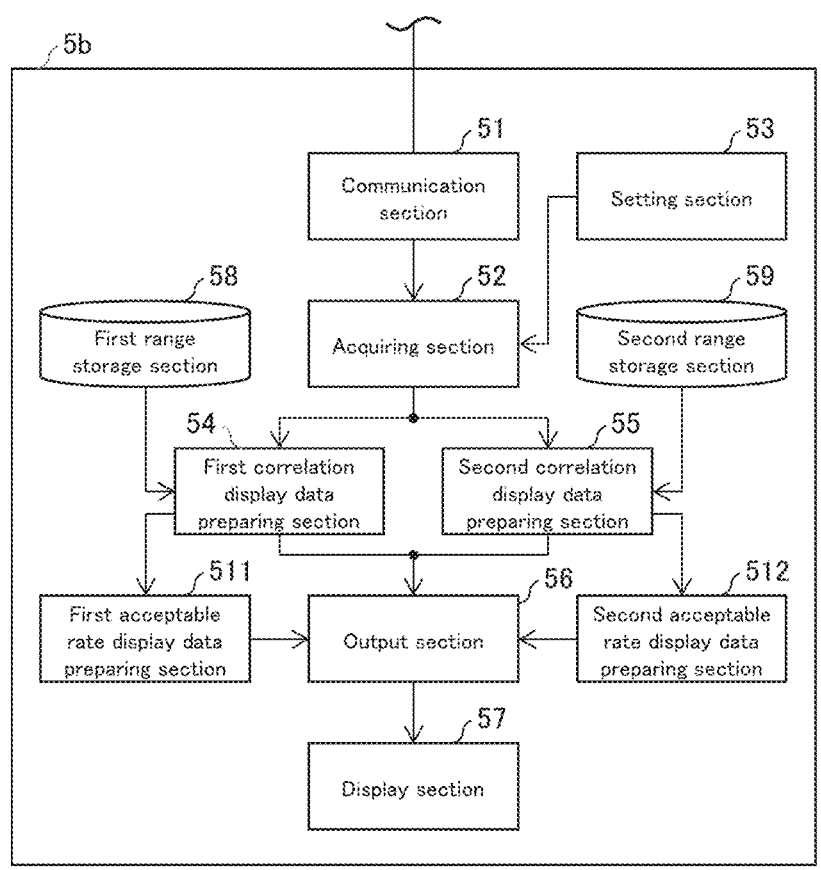

FIG. 10 is a block diagram illustrating a schematic configuration of a display apparatus in accordance with a further embodiment of the present invention.

DESCRIPTION OF EMBODIMENTS

Embodiment 1

The following description will discuss an embodiment of the present invention in detail.

Figure 1:
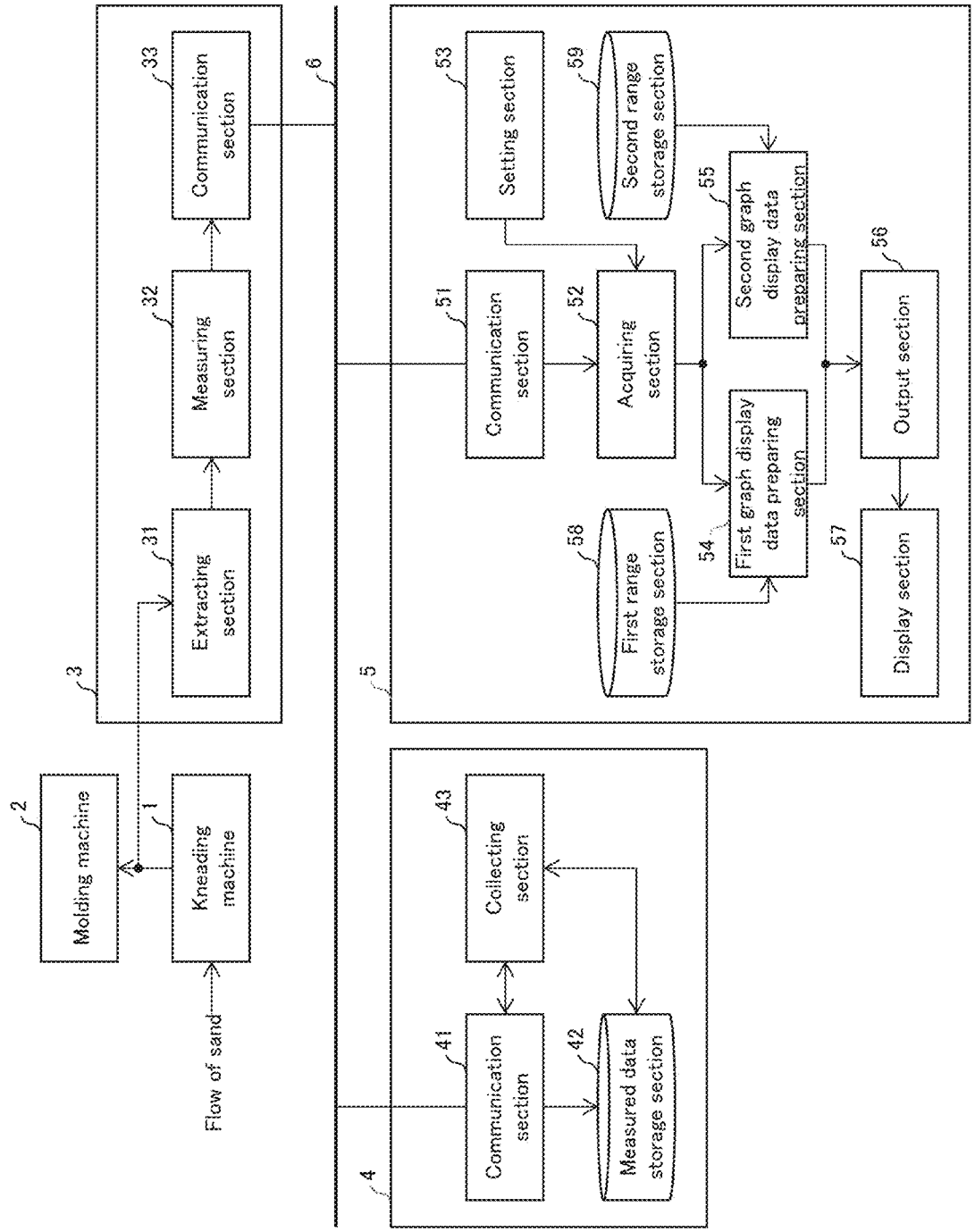
FIG. 1 illustrates a configuration of a system in accordance with an embodiment of the present invention.

(Overview of configuration) FIG. 1 illustrates a configuration of a system in accordance with Embodiment 1 of the present invention. As illustrated in FIG. 1, the system in accordance with Embodiment 1 includes a kneading machine 1, a molding machine 2, a measuring apparatus 3, a collecting apparatus 4, and a display apparatus 5. The measuring apparatus 3, the collecting apparatus 4, and the display apparatus 5 are capable of exchanging information and the like with each other through a communication network 6. Note that the communication network 6 can be the Internet, a local area network, or a wide area network.

Foundry sand for use in foundry molding is kneaded and conditioned in the kneading machine 1, then transferred to the molding machine 2, and is formed into a mold by the molding machine 2. Sand properties of the foundry sand change as the foundry sand is transferred from the kneading machine 1 to the molding machine 2 or change during the time interval between the completion of transfer to the molding machine 2 and the beginning of an actual molding step. Such a change in sand properties affects, for example, moldability to form a mold, and becomes a cause of a casting defect.

The measuring apparatus 3 extracts foundry sand immediately before the foundry sand is introduced into the molding machine 2, and measures sand properties of the extracted foundry sand. The sand properties measured by the measuring apparatus 3 are the following four sand properties: a first sand property; a second sand property; a third sand property; and a fourth sand property. In Embodiment 1, the first sand property is moisture content, the second sand property is compactability (CB), the third sand property is air permeability, and the fourth sand property is compressive strength.

The collecting apparatus 4 collects pieces of measured data obtained at the measuring apparatus 3 through the communication network 6, and stores the collected pieces of measured data such that each piece of measured data is associated with the date and time at which it was obtained. The pieces of measured data collected by the collecting apparatus 4 are those of the following four kinds of data: measured first sand property data; measured second sand property data; measured third sand property data; and measured fourth sand property data, each of which have been obtained as a time series. In Embodiment 1, the measured first sand property data is measured data obtained by measuring moisture content (hereinafter referred to as "measured moisture content data"), the measured second sand property data is measured data obtained by measuring CB (hereinafter referred to as "measured CB data", the measured third sand property data is measured data obtained by measuring air permeability (hereinafter referred to as "measured air permeability data"), and the measured fourth sand property data is measured data obtained by measuring compressive strength (hereinafter referred to as "measured compressive strength data").

The display apparatus 5 acquires the pieces of measured data from the collecting apparatus 4, and displays graphs prepared from the acquired pieces of measured data. The graphs displayed are the following two graphs: a first graph; and a second graph. In Embodiment 1, the first graph is a graph showing a relationship between measured first sand property data and measured second sand property data which were obtained as time series in a first predetermined period. That is, the first graph is a graph showing a relationship between measured moisture content data and measured CB data which were obtained as time series in the first predetermined period. Also, in Embodiment 1, the second graph is a graph showing a relationship between measured third sand property data and measured fourth sand property data which were obtained as time series in a second predetermined period. That is, the second graph is a graph showing a relationship between measured air permeability data and measured compressive strength data obtained in the second predetermined period. Note that the display apparatus 5 only needs to be configured to be communicable with the measuring apparatus 3 which measures the sand properties of the foundry sand, and the location of the display apparatus 5 can be changed as appropriate.

An example of the first graph is shown in (a) of FIG. 2. In the first graph shown in (a) of FIG. 2, a relationship between measured moisture content data and measured CB data, which were obtained in February, is shown as a scatter plot. Furthermore, in the first graph shown in (a) of FIG. 2, a reference range R3H-1 (range of from 3.3% to 3.5%, inclusive) set for moisture content is shown visually by displaying the range in a different manner (e.g., different color, different luminance) from the other portions. Moreover, in the first graph shown in (a) of FIG. 2, a reference range R3V-1 (range of from 32 to 38, inclusive) set for the CB is shown visually by displaying the range in a different manner from the other portions.

An example of the second graph is shown in (b) of FIG. 2. In the second graph shown in (b) of FIG. 2, a relationship between measured air permeability data and measured compressive strength data, which were obtained in February, is shown as a scatter plot. Furthermore, in the second graph shown in (b) of FIG. 2, a reference range R3H-2 (range of from 210 to 250, inclusive) set for air permeability is shown visually by displaying the range in a different manner from the other portions. Moreover, in the second graph shown in (b) of FIG. 2, a reference range R3V-2 (range of from 17 $N/cm^2$ to 20 $N/cm^2$, inclusive) set for compressive strength is shown visually by displaying the range in a different manner from the other portions.

(Measuring Apparatus)

As illustrated in FIG. 1, the measuring apparatus 3 includes an extracting section 31, a measuring section 32, and a communication section 33.

The extracting section 31 periodically samples the foundry sand while the foundry sand is being transferred from the kneading machine 1 to the molding machine 2 or during the time interval between the completion of transfer to the molding machine 2 and the beginning of the actual molding step. The measuring section 32 measures sand properties of the sampled foundry sand. The sand properties measured in Embodiment 1 are moisture content, CB, air permeability, and compressive strength. The communication section 33 transmits, to the collecting apparatus 4 through the communication network 6, pieces of measured CB data, pieces of measured moisture content data, pieces of measured air permeability data, and pieces of measured compressive strength data.

(Collecting Apparatus)

As illustrated in FIG. 1, the collecting apparatus 4 includes a communication section 41, a measured data storage section 42, and a collecting section 43.

The communication section 41 receives the pieces of measured CB data, the pieces of measured moisture content data, the pieces of measured air permeability data, and the pieces of measured compressive strength data, and the dates and times at which the respective pieces of each kind of measured data were obtained, which are transmitted from the communication section 33 of the measuring apparatus 3. The communication section 41 causes the measured data storage section 42 to store the received pieces of each kind of measured data and the dates and times at which the respective pieces of the measured data were obtained.

In accordance with a collection instruction transmitted from the display apparatus 5 through the communication network 6, the collecting section 43 collects, from the measured data storage section 42, pieces of measured data required by the display apparatus 5 and the dates and times at which the respective pieces of measured data were obtained. The collection instruction transmitted from the display apparatus 5 will be described later. The collecting section 43 transmits, to the communication section 41, the collected pieces of measured data and the dates and times at which the respective pieces of measured data were obtained. The communication section 41 transmits, to the display apparatus 5 through the communication network 6, the pieces of measured data and the dates and times at which the respective pieces of measured data were obtained, which have been collected by the collecting section 43.

(Display Apparatus)

As illustrated in FIG. 1, the display apparatus 5 includes a communication section 51, an acquiring section 52, a setting section 53, a first graph display data preparing section 54, a second graph display data preparing section 55, an output section 56, a display section 57, a first range storage section 58, and a second range storage section 59.

The setting section 53 includes a numeric keypad, keyboard, and/or the like, and information relating to measured data to be displayed on the display section 57 is inputted through the setting section 53. The information inputted is, specifically, as information relating to measured data to be displayed, (1) sand properties whose measured data are to be displayed, (2) a period of time in which measured data to be displayed were obtained, and (3) a combination of sand properties for which the relationship between their measured data is to be displayed.

The acquiring section 52 prepares, in accordance with the information inputted through the setting section 53, a collection instruction to be transmitted to the collecting apparatus 4, and outputs the collection instruction to the communication section 51. Specifically, the acquiring section 52 instructs, through the communication section 51, the collecting apparatus 4 to transmit, to the display apparatus 5, pieces of measured data and the dates and times at which the respective pieces of measured data were obtained which will be necessary for carrying out display on the display section 57 in accordance with the foregoing (1) to (3).

Once the acquiring section 52 acquires, from the collecting apparatus 4, the pieces of measured data and the dates and times at which the respective pieces of measured data were obtained, the acquiring section 52 outputs, to the first graph display data preparing section 54 and the second graph display data preparing section 55, the acquired pieces of measured data and the dates and times at which the respective pieces of measured data were obtained.

As described earlier, the display apparatus 5 displays (i) a first graph showing a relationship between measured first sand property data and measured second sand property data, i.e., a relationship between measured moisture content data and measured CB data, and (ii) a second graph showing a relationship between measured third sand property data and measured fourth sand property data, i.e., a relationship between measured air permeability data and measured compressive strength data. Note that the inventors of the present invention have discovered a process which, if carried out with respect to foundry sand when the moisture content and/or CB of the foundry sand have(has) changed and thereby exceeded the upper or lower limit thereof, is expected to bring the moisture content and CB each into its corresponding range including the upper and lower limits. Similarly, the inventors have discovered a process which, if carried out with respect to foundry sand when the air permeability and/or compressive strength of the foundry sand have(has) changed and thereby exceeded the upper or lower limit thereof, is expected to bring the air permeability and compressive strength each into its corresponding range including the upper and lower limits.

Pieces of measured moisture content data, pieces of measured CB data, pieces of measured air permeability data, and pieces of measured compressive strength data are pieces of data obtained as time series in the same measurement period. More specifically, pieces of measured moisture content data, pieces of measured CB data, pieces of measured air permeability data, and pieces of measured compressive strength data are pieces of measured data obtained by measuring foundry sand periodically sampled at the measuring apparatus 3, and can be said to be pieces of data obtained by periodically carrying out measurement as time passes.

Note that, with regard to a measurement period inputted through the setting section 53 (pieces of measured data obtained in this period are to be displayed), it is only necessary that the measurement period be the same between two sand properties for which the relationship between their measured data is shown in a graph. More specifically, it is only necessary that (i) measurement periods for measured moisture content data and measured CB data (the relationship between which is shown in the first graph) be the same measurement period (first predetermined period) and (ii) measurement periods for measured air permeability data and measured compressive strength data (the relationship between which is shown in the second graph) be the same measurement period (second predetermined period).

Specifically, the acquiring section 52 outputs the pieces of measured moisture content data and the pieces of measured CB data to the first graph display data preparing section 54, and outputs the pieces of measured air permeability data and the pieces of measured compressive strength data to the second graph display data preparing section 55.

The first graph display data preparing section 54, on the basis of the pieces of measured moisture content data and the pieces of measured CB data inputted thereto, prepares first graph display data which is for use in displaying, on the display section 57, the first graph showing the relationship between the measured moisture content data and the measured CB data. On the first graph, all pieces of measured moisture content data and all pieces of measured CB data obtained in the measurement period inputted through the setting section 53 are plotted.

Note, here, that the pieces of measured data plotted on the first graph do not necessarily need to be all pieces of measured data obtained in the measurement period inputted through the setting section 53. It is only necessary that a sufficient number of pieces of measured moisture content data and a sufficient number of pieces of measured CB data, which are sufficient to show the relationship between the measured moisture content data and the measured CB data, be plotted on the first graph. Note that, in Embodiment 1, the following description is based on the assumption that all pieces of measured moisture content data and all pieces of measured CB data obtained in the measurement period inputted through the setting section 53 are plotted on the first graph.

The first range storage section 58 stores therein upper and lower limits data for moisture content of foundry sand and upper and lower limits data for CB of the foundry sand. The first graph display data preparing section 54 acquires, from the first range storage section 58, the upper and lower limits data for moisture content and the upper and lower limits data for CB, and adds the acquired upper and lower limits data for moisture content and the upper and lower limits data for CB to the first graph.

The first graph display data preparing section 54 outputs the prepared first graph display data to the output section 56.

The upper and lower limits data for moisture content of foundry sand and the upper and lower limits data for CB of the foundry sand are calculated from a relationship between (i) previously measured moisture content data and previously measured CB data and (ii) defect rate of castings produced during a period in which those measured data were obtained. Note that the upper and lower limits data for moisture content of foundry sand and the upper and lower limits data for CB of the foundry sand may be calculated based on a relationship between (a) previously measured moisture content data and previously measured CB data and (b) defect rate of molds, in addition to or instead of the relationship between (i) previously measured moisture content data and previously measured CB data and (ii) defect rate of castings.

Alternatively, the upper and lower limits data for moisture content of foundry sand and the upper and lower limits data for CB of the foundry sand may be calculated with use of a pre-trained model which is constructed by machine learning using training data generated from previously measured moisture content data and previously measured CB data. It is preferable that the pre-trained model is constructed by supervised learning.

The second graph display data preparing section 55, on the basis of the pieces of measured air permeability data and the pieces of measured compressive strength data inputted thereto, prepares second graph display data for use in displaying, on the display section 57, the second graph showing the relationship between the measured air permeability data and the measured compressive strength data. On the second graph, all pieces of measured air permeability data and all pieces of measured compressive strength data obtained in the measurement period inputted through the setting section 53 are plotted.

Note, here, that the pieces of measured data plotted on the second graph do not necessarily need to be all pieces of measured data obtained in the measurement period inputted through the setting section 53. It is only necessary that a sufficient number of pieces of measured air permeability data and a sufficient number of pieces of measured compressive strength data, which are sufficient to show the relationship between the measured air permeability data and the measured compressive strength data, be plotted on the second graph. Note that, in Embodiment 1, the following description is based on the assumption that all pieces of measured air permeability data and all pieces of measured compressive strength data obtained in the measurement period inputted through the setting section 53 are plotted on the second graph.

The second range storage section 59 stores therein upper and lower limits data for air permeability of foundry sand and upper and lower limits data for compressive strength of the foundry sand. The second graph display data preparing section 55 acquires, from the second range storage section 59, the upper and lower limits data for air permeability and the upper and lower limits data for compressive strength, and adds the acquired upper and lower limits data for air permeability and the upper and lower limits data for compressive strength to the second graph.

The second graph display data preparing section 55 outputs the prepared second graph display data to the output section 56.

The upper and lower limits data for air permeability of foundry sand and the upper and lower limits data for compressive strength of the foundry sand are calculated from a relationship between (i) previously measured air permeability data and previously measured compressive strength data and (ii) defect rate of castings produced during a period in which those measured data were obtained. Note that the upper and lower limits data for air permeability of foundry sand and the upper and lower limits data for compressive strength of the foundry sand may be calculated based on a relationship between (a) previously measured air permeability data and previously measured compressive strength data and (b) defect rate of molds, in addition to or instead of the relationship between (i) previously measured air permeability data and previously measured compressive strength data and (ii) defect rate of castings.

Alternatively, the upper and lower limits data for air permeability of foundry sand and the upper and lower limits data for compressive strength of the foundry sand may be calculated with use of a pre-trained model which is constructed by machine learning using training data generated from previously measured air permeability data and previously measured compressive strength data. It is preferable that the pre-trained model is constructed by supervised learning.

The output section 56 outputs, to the display section 57, the first graph display data and the second graph display data inputted thereto. The display section 57 includes a display area (not illustrated), and displays the first graph and the second graph in the display area on the basis of the first graph display data and the second graph display data inputted from the output section 56.

It should be noted here that the display section 57 displays, in a single display area, the first graph showing the relationship between the measured moisture content data and the measured CB data and the second graph showing the relationship between the measured air permeability data and the measured compressive strength data.

Specifically, the first graph shows a relationship between all pieces of measured moisture content data and all pieces of measured CB data obtained in the measurement period inputted through the setting section 53. The all pieces of measured moisture content data and the all pieces of measured CB data are, as described earlier, pieces of data measured as time series. Furthermore, the second graph shows a relationship between all pieces of measured air permeability data and all pieces of measured compressive strength data obtained in the measurement period inputted through the setting section 53. The all pieces of measured air permeability data and the all pieces of measured compressive strength data are, as described earlier, pieces of data measured as time series.

Since these two graphs (first graph and second graph) are displayed in a single display area, it is possible to provide the following advantages to a user. Note that the first graph and the second graph may be displayed in a single display area in the following manner: the first graph and the second graph are adjacent to each other along the vertical direction of the display area; or the first graph and the second graph are adjacent to each other along the horizontal direction of the display area.

(1) Assume that the moisture content and/or CB have(has) changed and thereby exceeded the upper or lower limit thereof, and that a process which is expected to bring the moisture content and CB each into its corresponding range including the upper and lower limits has been carried out. In this case, the user can check whether or not the process affects air permeability and/or compressive strength. Similarly, assume that the air permeability and/or compressive strength have(has) changed and thereby exceeded the upper or lower limit thereof, and that a process which is expected to bring the air permeability and compressive strength each into its corresponding range including the upper and lower limits has been carried out. In this case, the user can check whether or not the process affects moisture content and/or CB.

(2) Assume that the moisture content and/or CB have(has) changed and thereby exceeded the upper or lower limit thereof, and that a process which is expected to bring the moisture content and CB each into its corresponding range including the upper and lower limits has been carried out. In this case, the user can check how the moisture content, CB, air permeability, and compressive strength will change as time passes after the process is carried out. Similarly, assume that the air permeability and/or compressive strength have (has) changed and thereby exceeded the upper or lower limit thereof, and that a process which is expected to bring the air permeability and compressive strength each into its corresponding range including the upper and lower limits has been carried out. In this case, the user can check how the moisture content, CB, air permeability, and compressive strength will change as time passes after the process is carried out.

(Operation of Display Apparatus)

(a) of FIG. 3 is a graph showing measured CB data, (b) of FIG. 3 is a graph showing measured moisture content data, (c) of FIG. 3 is a graph showing measured air permeability data, and (d) of FIG. 3 is a graph showing measured compressive strength data. In the graphs shown in (a) to (d) of FIG. 3, reference ranges R21, R22, R23, and R24, each of which includes the upper and lower limits of a corresponding sand property, are shown, respectively. The reference ranges R21, R22, R23, and R24 are reference ranges for CB, moisture content, air permeability, and compressive strength, respectively.

(a) of FIG. 4 is a graph showing a relationship between measured moisture content data and measured CB data, and (b) of FIG. 4 is a graph showing a relationship between measured air permeability data and measured compressive strength data. In the graphs shown in (a) and (b) of FIG. 4, reference ranges R3H-1, R3V-1, R3H-2, and R3V-2, each of which includes the upper and lower limits of a corresponding sand property, are shown. The reference ranges R3H-1, R3V-1, R3H-2, and R3V-2 are reference ranges for moisture content, CB, air permeability, and compressive strength, respectively (such reference ranges are first to fourth reference ranges).

In each of the graphs of (a) to (d) of FIG. 3, whether or not the measured data obtained by measuring a sand property is within the reference range R21, R22, R23, or R24 is displayed on a per-sand-property basis.

In contrast, the display apparatus 5 displays, in a single display area of the display section 57, the graphs shown in (a) and (b) of FIG. 4 as the foregoing first graph and second graph. Specifically, the display apparatus 5 displays, in a single display area, (i) a relationship between measured moisture content data and measured CB data and (ii) a relationship between measured air permeability data and measured compressive strength data.

Furthermore, the display apparatus 5 displays remedial measure assistance information in the same display area of the display section 57. The remedial measure assistance information is indicative of a process to be carried out, in a case where at least one sand property has exceeded the upper or lower limit of its reference range (i.e., corresponding one of the first to fourth reference ranges), in order to bring the at least one sand property (which has exceeded the upper or lower limit of its reference range) into that reference range. For example, in a case where moisture content has exceeded the lower limit of the reference range R3H-1 and CB has exceeded the upper limit of the reference range R3V-1, if the process "Reduce new sand, increase fine powder" is carried out, it is expected that moisture content will be brought into the reference range R3H-1 and CB will be brought into the reference range R3V-1. In view of this, as shown in (a) of FIG. 4, remedial measure assistance information P1-1, which is indicative of such a process, is displayed. On the other hand, in a case where moisture content has exceeded the upper limit of the reference range R3H-1 and CB has exceeded the lower limit of the reference range R3V-1, if the process "Increase new sand, reduce fine powder" is carried out, it is expected that moisture content will be brought into the reference range R3H-1 and CB will be brought into the reference range R3V-1. In view of this, as shown in (a) of FIG. 4, remedial measure assistance information P1-2, which is indicative of such a process, is displayed.

Furthermore, in a case where CB has exceeded the upper limit of the reference range R3V-1, if the process "Reduce moisture content" is carried out, it is expected that CB will be brought into the reference range R3V-1. In view of this, as shown in (a) of FIG. 4, remedial measure assistance information P2-1, which is indicative of such a process, is displayed. On the other hand, in a case where CB has exceeded the lower limit of the reference range R3V-1, if the process "Increase moisture content" is carried out, it is expected that CB will be brought into the reference range R3V-1. In view of this, as shown in (a) of FIG. 4, remedial measure assistance information P2-2, which is indicative of such a process, is displayed.

Moreover, in a case where moisture content has exceeded the lower limit of the reference range R3H-1, if the process "Increase moisture content" is carried out, it is expected that moisture content will be brought into the reference range R3H-1. In view of this, as shown in (a) of FIG. 4, remedial measure assistance information P3-1, which is indicative of such a process, is displayed. On the other hand, in a case where moisture content has exceeded the upper limit of the reference range R3H-1, if the process "Reduce moisture content" is carried out, it is expected that moisture content will be brought into the reference range R3H-1. In view of this, as shown in (a) of FIG. 4, remedial measure assistance information P3-2, which is indicative of such a process, is displayed.

Moreover, in a case where compressive strength has exceeded the upper limit of the reference range R3V-2, if the process "Reduce bentonite" is carried out, it is expected that compressive strength will be brought into the reference range R3V-2. In view of this, as shown in (b) of FIG. 4, remedial measure assistance information P4-1, which is indicative of such a process, is displayed. On the other hand, in a case where compressive strength has exceeded the lower limit of the reference range R3V-2, if the process "Increase bentonite" is carried out, it is expected that compressive strength will be brought into the reference range R3V-2. In view of this, as shown in (b) of FIG. 4, remedial measure assistance information P4-2, which is indicative of such a process, is displayed.

Moreover, in a case where air permeability has exceeded the lower limit of the reference range R3H-2, if the process "Increase new sand, reduce fine powder" is carried out, it is possible to bring air permeability into the reference range R3H-2. In view of this, as shown in (b) of FIG. 4, remedial measure assistance information P5-1, which is indicative of such a process, is displayed. On the other hand, in a case where air permeability has exceeded the upper limit of the reference range R3H-2, if the process "Reduce new sand, increase fine powder" is carried out, it is possible to bring air permeability into the reference range R3H-2. In view of this, as shown in (b) of FIG. 4, remedial measure assistance information P5-2, which is indicative of such a process, is displayed.

The following description will discuss operation of the display apparatus 5 with reference to graphs shown in (a) to (c) of FIG. 5. According to the graphs shown in (a) and (b) of FIG. 5, CB has exceeded the lower limit of its reference range (area enclosed by solid line in (a) of FIG. 5), and moisture content has exceeded the upper limit of its reference range (area enclosed by solid line in (b) of FIG. 5). In this case, it is expected that, by carrying out the process "Increase moisture content" in accordance with remedial measure assistance information P11-1 displayed on the graph shown in (a) of FIG. 5, CB will be brought into its reference range. On the contrary, it is expected that, by carrying out the process "Reduce moisture content" in accordance with remedial measure assistance information P11-2 displayed on the graph shown in (b) of FIG. 5, moisture content will be brought into its reference range.

However, it is apparent that the process "Increase moisture content" based on the graph shown in (a) of FIG. 5 and the process "Reduce moisture content" based on the graph shown in (b) of FIG. 5 cannot be carried out simultaneously.

In contrast, according to the graph shown in (c) of FIG. 5, moisture content has exceeded the upper limit of the reference range R3H-1, and CB has exceeded the lower limit of the reference range R3V-1. In this case, it is expected that, by carrying out the process "Increase new sand, reduce fine powder" in accordance with remedial measure assistance information P1-2, moisture content will be brought into the reference range R3H-1 and CB will be brought into the reference range R3V-1.

As such, according to the graph shown in (c) of FIG. 5, it is possible to display the remedial measure assistance information P1-2 which corresponds to the process "Increase new sand, reduce fine powder" that is expected to bring moisture content into the reference range R3H-1 and bring CB into the reference range R3V-1.

(a) of FIG. 6 is a graph showing a relationship between measured moisture content data and measured CB data, and (b) of FIG. 6 is a graph showing a relationship between measured air permeability data and measured compressive strength data. As described earlier, in a case where moisture content has exceeded the upper limit of the reference range R3H-1 and CB has exceeded the lower limit of the reference range R3V-1, if the process "Increase new sand, reduce fine powder" is carried out in accordance with the remedial measure assistance information P1-2, it is expected that the measured data distribution will move as indicated by the arrow in (a) of FIG. 6, and that moisture content will be brought into the reference range R3H-1 and CB will be brought into the reference range R3V-1.

Moreover, according to the graph shown in (b) of FIG. 6, when the process "Increase new sand, reduce fine powder" is carried out in accordance with remedial measure assistance information P1-2, it is expected that air permeability will be brought into the reference range R3H-2 as indicated by the arrow in (b) of FIG. 6.

As such, according to the graph shown in (b) of FIG. 6, it is possible to bring air permeability into the reference range R3H-2.

Embodiment 2

As has been described, it is preferable that, on the first graph and the second graph, various kinds of remedial measure assistance information which assist a user in taking remedial measures with respect to foundry sand are displayed as needed. The following description will discuss Embodiment 2, which is suitable for displaying various kinds of remedial measure assistance information. Note that, for convenience of description, members having functions identical to those described in Embodiment 1 are assigned identical referential numerals, and their descriptions are not repeated. Also note that a display apparatus 5 in accordance with Embodiment 2 is referred to as "display apparatus 5a" for distinction from the display apparatus 5 in accordance with Embodiment 1.

FIG. 9 is a block diagram illustrating a schematic configuration of the display apparatus 5a in accordance with Embodiment 2. The display apparatus 5a in accordance with Embodiment 2 is different from the display apparatus 5 in accordance with Embodiment 1 in that the display apparatus 5a further includes a remedial measure assistance information preparing section 501 and a remedial measure storage section 502.

The remedial measure assistance information preparing section 501 prepares remedial measure assistance information data which is for use in displaying remedial measure assistance information on the display section 57. The remedial measure assistance information is indicative of a process to be carried out, in a case where at least one of the sand properties such as CB and moisture content has exceeded the upper or lower limit of its reference range (i.e., corresponding one of the first to fourth reference ranges), in order to bring the at least one sand property (which has exceeded the upper or lower limit of its reference range) into that reference range.

The remedial measure assistance information preparing section 501 outputs the prepared remedial measure assistance information data to the output section 56. The output section 56 outputs the inputted remedial measure assistance information data to the display section 57. The display section 57 displays, in the display area, a first graph, a second graph, and the remedial measure assistance information on the basis of first graph display data, second graph display data, and the remedial measure assistance information data which have been inputted from the output section 56 (see (a) and (b) of FIG. 4).

The remedial measure storage section 502 stores various kinds of remedial measure assistance information therein. The various kinds of remedial measure assistance information stored in the remedial measure storage section 502 are indicative of processes such as P1-1 described in Embodiment 1. The remedial measure assistance information preparing section 501 acquires, from the remedial measure storage section 502, remedial measure assistance information which best suits for bringing at least one sand property that has exceeded the upper or lower limit of its reference range into the reference range.

As such, it is possible to display remedial measure assistance information and the first and second graphs in a single display area.

Embodiment 3

The following description will discuss a further embodiment of the present invention. Note that, for convenience of description, members having functions identical to those described in Embodiments 1 and 2 are assigned identical referential numerals, and their descriptions are not repeated.

FIG. 10 is a block diagram illustrating a schematic configuration of a display apparatus 5b in accordance with Embodiment 3. The display apparatus 5b in accordance with Embodiment 3 is different from the display apparatus 5 in accordance with Embodiment 1 in that the display apparatus 5b further includes a first acceptable rate display data preparing section 511 and a second acceptable rate display data preparing section 512.

The first acceptable rate display data preparing section 511 prepares first acceptable rate display data on the basis of first graph display data inputted from the first graph display data preparing section 54. The first acceptable rate display data is for use in displaying a first acceptable rate for each predetermined period. The first acceptable rate is the probability that a value of measured moisture content data is within a reference range for moisture content and a value of measured CB data is within a reference range for CB.

The second acceptable rate display data preparing section 512 prepares second acceptable rate display data on the basis of second graph display data inputted from the second graph display data preparing section 55. The second acceptable rate display data is for use in displaying a second acceptable rate for each predetermined period. The second acceptable rate is the probability that a value of measured air permeability data is within a reference range for air permeability and a value of measured compressive strength data is within a reference range for compressive strength.

The first acceptable rate display data preparing section 511 outputs the prepared first acceptable rate display data to the output section 56. The second acceptable rate display data preparing section 512 outputs the prepared second acceptable rate display data to the output section 56. The output section 56 outputs the inputted first acceptable rate display data and second acceptable rate display data to the display section 57. The display section 57 displays, in the display area, a first graph, a second graph, the first acceptable rate display data, and the second acceptable rate display data on the basis of first graph display data, second graph display data, the first acceptable rate display data, and the second acceptable rate display data which have been inputted from the output section 56.

(a) of FIG. 7 is a graph showing a relationship between measured moisture content data and measured CB data. (b) of FIG. 7 is a graph showing acceptable rate which is the probability that a value of measured moisture content data and a value of measured CB data are both within respective predetermined reference ranges. (c) of FIG. 7 is a graph showing a relationship between measured air permeability data and measured compressive strength data. (d) of FIG. 7 is a graph showing acceptable rate which is the probability that a value of measured air permeability data and a value of measured compressive strength data are both within respective predetermined reference ranges.

In the graph shown in (b) of FIG. 7, a high acceptable rate is seen on the date indicated by the letter X. In the graph shown in (d) of FIG. 7, a high acceptable rate is seen on the date indicated by the letter Y.

(a) of FIG. 8 is a graph showing acceptable rate which is the probability that a value of measured moisture content data and a value of measured CB data are both within respective predetermined reference ranges. (b) of FIG. 8 is a graph showing acceptable rate which is the probability that a value of measured air permeability data and a value of measured compressive strength data are both within respective predetermined reference ranges. (c) of FIG. 8 is a graph showing measured data obtained by measuring air flow rate of a dust collector.

From the graph of (a) of FIG. 8, a user understands that a reduction has occurred in an acceptable rate which is the probability that a value of measured moisture content data and a value of measured CB data are both within respective predetermined reference ranges (S1). From the graph of (b) of FIG. 8, the user understands that a reduction has occurred in an acceptable rate which is the probability that a value of measured air permeability data and a value of measured compressive strength data are both within respective predetermined reference ranges (S2). The user then recognizes that some phenomenon has occurred and thereby induced the reductions in acceptable rates (S3). Note that, both in (a) and (b) of FIG. 8, the acceptable rate on April 17 (April-17) is lower than the acceptable rate on February 17 (February-17).

The user can make a judgement, from the foregoing graphs of (a) and (b) of FIG. 6, that such reductions in acceptable rates have resulted from an increase in fine powder. This makes it possible to determine that such an increase in fine powder is a phenomenon that has induced reductions in acceptable rates.

The user can determine, from the graph of (c) of FIG. 8, that a reduction in air flow rate of the dust collector is a cause of the above increase in fine powder (S4).

Note that the display apparatus 5b may include a first unacceptable rate display data preparing section in addition to or instead of the first acceptable rate display data preparing section 511. As used herein, the "first unacceptable rate display data preparing section" is a block that prepares first unacceptable rate display data for use in displaying a first unacceptable rate for each predetermined period on the basis of first graph display data inputted from the first graph display data preparing section 54. The first unacceptable rate is the probability that a value of measured moisture content data is outside a reference range for moisture content or a value of measured CB data is outside a reference range for CB. Also note that the display apparatus 5b may include a second unacceptable rate display data preparing section in addition to or instead of the second acceptable rate display data preparing section 512. As used herein, the "second unacceptable rate display data preparing section" is a block that prepares second unacceptable rate display data for use in displaying a second unacceptable rate for each predetermined period on the basis of second graph display data inputted from the second graph display data preparing section 55. The second unacceptable rate is the probability that a value of measured air permeability data is outside a reference range for air permeability or a value of measured compressive strength data is outside a reference range for compressive strength. In this case, the output section 56 outputs, to the display section 57, the first unacceptable rate display data and the second unacceptable rate display data which have been acquired from the first unacceptable rate display data preparing section and the second unacceptable rate display data preparing section, respectively. The display section 57 displays, in the display area, a first graph, a second graph, the first unacceptable rate display data, and the second unacceptable rate display data, on the basis of the first graph display data, the second graph display data, the first acceptable rate display data, and the second acceptable rate display data which have been inputted from the output section 56.

Variations

Embodiments 1 to 3 described so far each employ a configuration in which a first graph and a second graph are displayed in a display area of a single display section 57; however, the present invention is not limited as such. For example, the following arrangement may be employed: a single display section 57 is provided with two adjacent display areas; the first graph is displayed in one of the display areas; and the second graph is displayed in the other of the display areas. Alternatively, the following arrangement may be employed: two adjacent display sections 57 are provided; the first graph is displayed on one of the display sections 57; and the second graph is displayed on the other of the display sections 57. Provided that the display area in which the first graph is displayed and the display area in which the second graph is displayed are adjacent to each other as such, it is possible to obtain effects which are similar to those achieved in a case where the first graph and the second graph are displayed in a single display area.

Furthermore, Embodiments 1 to 3 described so far each employ a configuration in which measured first sand property data is measured moisture content data, measured second sand property data is measured CB data, measured third sand property data is measured air permeability data, and measured fourth sand property data is measured compressive strength data; however, the present invention is not limited as such. For example, the combination of the measured first sand property data and the measured second sand property data can be a first combination consisting of two kinds of measured data obtained by measuring respective two sand properties selected from moisture content, CB, air permeability, and compressive strength. In this case, the combination of the measured third sand property data and the measured fourth sand property data can be a second combination which consists of two kinds of measured data obtained by measuring respective two sand properties selected from moisture content, CB, air permeability, and compressive strength and which is different from the first combination.

Software Implementation Example

Control blocks of the display apparatus 5, 5a, 5b (particularly, the acquiring section 52, the setting section 53, the first graph display data preparing section 54, the second graph display data preparing section 55, the output section 56, the remedial measure assistance information preparing section 501, the first acceptable rate display data preparing section 511, and the second acceptable rate display data preparing section 512) can be realized by a logic circuit (hardware) provided in an integrated circuit (IC chip) or the like or can be alternatively realized by software.

In the latter case, the display apparatus 5, 5a, 5b includes a computer that executes instructions of a program that is software realizing the foregoing functions. The computer, for example, includes at least one processor and at least one computer-readable storage medium storing the program. An object of the present invention can be achieved by the processor of the computer reading and executing the program stored in the storage medium. Examples of the processor encompass a central processing unit (CPU). Examples of the storage medium encompass a "non-transitory tangible medium" such as a read only memory (ROM), a tape, a disk, a card, a semiconductor memory, and a programmable logic circuit. The computer may further include a random access memory (RAM) or the like in which the program is loaded. Further, the program may be made available to the computer via any transmission medium (such as a communication network and a broadcast wave) which allows the program to be transmitted. Note that an aspect of the present invention can also be achieved in the form of a computer data signal in which the program is embodied via electronic transmission and which is embedded in a carrier wave.

Aspects of the present invention can also be expressed as follows.

In order to attain the foregoing object, a display apparatus in accordance with an aspect of the present invention is a display apparatus configured to display sand properties of foundry sand, including: a first graph display data preparing section configured to (i) acquire, from a storage device which stores therein pieces of measured data obtained by measuring each of sand properties as a time series and dates and times at which the respective pieces of measured data were obtained, pieces of measured first sand property data which were obtained in a first predetermined period and pieces of measured second sand property data which were obtained in the first predetermined period, and (ii) prepare first graph display data for use in displaying a first graph together with a first reference range and a second reference range, the first graph showing a relationship between the pieces of measured first sand property data and the pieces of measured second sand property data, the first reference range having been set for a first sand property, the second reference range having been set for a second sand property; a second graph display data preparing section configured to (a) acquire, from the storage device, pieces of measured third sand property data which were obtained in a second predetermined period and pieces of measured fourth sand property data which were obtained in the second predetermined period, and (b) prepare second graph display data for use in displaying a second graph together with a third reference range and a fourth reference range, the second graph showing a relationship between the pieces of measured third sand property data and the pieces of measured fourth sand property data, the third reference range having been set for a third sand property, the fourth reference range having been set for a fourth sand property; and a display section which includes a display area and which is configured to display the first graph and the second graph in the display area on the basis of the first graph display data and the second graph display data.

The configuration makes it possible to display a relationship between sand properties measured as time series.

A combination of the measured first sand property data and the measured second sand property data is preferably a first combination which consists of two kinds of measured data obtained by measuring respective two sand properties selected from moisture, compactability (CB), air permeability, and compressive strength. A combination of the measured third sand property data and the measured fourth sand property data is preferably a second combination which consists of two kinds of measured data obtained by measuring respective two sand properties selected from moisture content, CB, air permeability, and compressive strength and which is different from the first combination.

The configuration makes it possible to display, on the display section, (i) a relationship between measured moisture content data and measured CB data and (ii) a relationship between measured air permeability data and measured compressive strength data.

It is preferable that: the measured first sand property data is measured data obtained by measuring moisture content; the measured second sand property data is measured data obtained by measuring compactability (CB); the measured third sand property data is measured data obtained by measuring air permeability; and the measured fourth sand property data is measured data obtained by measuring compressive strength.

The configuration makes it possible to display, on the display section, (i) a relationship between measured moisture content data and measured CB data and (ii) a relationship between measured air permeability data and measured compressive strength data.

It is preferable that the display apparatus further includes: a first acceptable rate display data preparing section configured to prepare first acceptable rate display data for use in displaying a first acceptable rate for each of a plurality of the first predetermined periods, the first acceptable rate being a probability that a value of the measured first sand property data is within the first reference range and a value of the measured second sand property data is within the second reference range; and a second acceptable rate display data preparing section configured to prepare second acceptable rate display data for use in displaying a second acceptable rate for each of a plurality of the second predetermined periods, the second acceptable rate being a probability that a value of the measured third sand property data is within the third reference range and a value of the measured fourth sand property data is within the fourth reference range, wherein the display section is configured to further display the first acceptable rate display data and the second acceptable rate display data in the display area in which the first graph and the second graph are displayed.

The configuration makes it possible to easily understand the acceptable rate of measured data obtained by measuring each sand property.

The display apparatus further includes: a first unacceptable rate display data preparing section configured to prepare first unacceptable rate display data for use in displaying a first unacceptable rate for each of a plurality of the first predetermined periods, the first unacceptable rate being a probability that a value of the measured first sand property data is outside the first reference range or a value of the measured second sand property data is outside the second reference range; and a second unacceptable rate display data preparing section configured to prepare second unacceptable rate display data for use in displaying a second unacceptable rate for each of a plurality of the second predetermined periods, the second unacceptable rate being a probability that a value of the measured third sand property data is outside the third reference range or a value of the measured fourth sand property data is outside the fourth reference range. It is preferable that the display section is configured to further display the first unacceptable rate display data and the second unacceptable rate display data in the display area in which the first graph and the second graph are displayed.

The configuration makes it possible to easily understand the unacceptable rate of measured data obtained by measuring each sand property.

It is preferable that the display apparatus further includes: a first storage section configured to pre-store the first reference range and the second reference range therein; and a second storage section configured to pre-store the third reference range and the fourth reference range therein.

It is preferable that the display apparatus further includes a remedial measure assistance information preparing section configured to prepare remedial measure assistance information which assists a user in taking a remedial measure with respect to foundry sand, wherein the remedial measure assistance information is prepared in accordance with: whether or not the measured first sand property data is within the first reference range, and, whether or not the measured second sand property data is within the second reference range; and whether or not the measured third sand property data is within the third reference range, and, whether or not the measured fourth sand property data is within the fourth reference range.

The configuration makes it possible to provide remedial measure assistance information which assists a user in taking a remedial measure with respect to foundry sand.

It is preferable that: the remedial measure assistance information preparing section is configured to prepare the remedial measure assistance information as display data to be displayed in the display area; and the display section is configured to display the remedial measure assistance information in the display area in which the first graph and the second graph are displayed.

The configuration makes it possible to easily understand the remedial measure assistance information which assists a user in taking a remedial measure with respect to foundry sand.

It is preferable that the display apparatus further includes a storage section configured to pre-store the remedial measure assistance information therein.

A display apparatus in accordance with each aspect of the present invention can be realized by a computer. The computer is operated based on (i) a display apparatus control program for causing the computer to realize the display apparatus by causing the computer to operate as each section included in the display apparatus and (ii) a computer-readable storage medium in which the display apparatus control program is stored. Such a control program and a computer-readable storage medium are included in the scope of the present invention. The display apparatus in accordance with each aspect of the present invention may be realized as an integrated circuit (IC chip). A chip including the integrated circuit, and the like, are also included in the scope of the present invention.

REMARKS

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST 1 kneading machine
2 molding machine
3 measuring apparatus
4 collecting apparatus
5, 5a, 5b display apparatus
6 communication network
31 extracting section
32 measuring section
33 communication section
41 communication section
42 measured data storage section
43 collecting section
51 communication section
52 acquiring section
53 setting section
54 first graph display data preparing section
55 second graph display data preparing section
56 output section
57 display section
58 first range storage section
59 second range storage section
501 remedial measure assistance information preparing section
502 remedial measure storage section
511 first acceptable rate display data preparing section
512 second acceptable rate display data preparing section

The invention claimed is:

1. A display apparatus configured to display sand properties of foundry sand, comprising:
at least one processor configured to carry out
a first graph display data preparing process of
(i) acquiring, from a storage device which stores therein pieces of measured data obtained by measuring each of sand properties as a time series and dates and times at which the respective pieces of measured data were obtained, pieces of measured first sand property data which were obtained in a first predetermined period and pieces of measured second sand property data which were obtained in the first predetermined period, and
(ii) preparing first graph display data for use in displaying a first graph together with a first reference range and a second reference range, the first graph being a scatter diagram showing a relationship between the pieces of measured first sand property data and the pieces of measured second sand property data, the first reference range having been set for a first sand property, the second reference range having been set for a second sand property,
a second graph display data preparing process of
(a) acquiring, from the storage device, pieces of measured third sand property data which were obtained in a second predetermined period and pieces of measured fourth sand property data which were obtained in the second predetermined period, and
(b) preparing second graph display data for use in displaying a second graph together with a third reference range and a fourth reference range, the second graph being a scatter diagram showing a relationship between the pieces of measured third sand property data and the pieces of measured fourth sand property data, the third reference range having been set for a third sand property, the fourth reference range having been set for a fourth sand property, and
a remedial measure assistance information preparing process of preparing remedial measure assistance information which assists a user in taking a remedial measure with respect to foundry sand so that the measured first sand property data is within the first reference range, the measured second sand property data is within the second reference range, the measured third sand property data is within the third reference range, and the measured fourth sand property data is within the fourth reference range; and
a display section which includes a display area and which is configured to display the first graph and the second graph in the display area on the basis of the first graph display data and the second graph display data,
a combination of the measured first sand property data and the measured second sand property data being a first combination which consists of two kinds of measured data obtained by measuring respective two sand properties selected from moisture content, compactability (CB), air permeability, and compressive strength, and
a combination of the measured third sand property data and the measured fourth sand property data being a second combination which consists of two kinds of measured data obtained by measuring respective two sand properties selected from moisture content, CB, air permeability, and compressive strength and which is different from the first combination, the at least one processor being configured to prepare, in the remedial measure assistance information preparing process, the remedial measure assistance information as display data to be displayed in the display area, and the display section being configured to display the remedial measure assistance information in the display area in which the first graph and the second graph are displayed.

2. The display apparatus according to claim 1, wherein:
the measured first sand property data is measured data obtained by measuring moisture content;
the measured second sand property data is measured data obtained by measuring compactability;
the measured third sand property data is measured data obtained by measuring air permeability; and
the measured fourth sand property data is measured data obtained by measuring compressive strength.

3. The display apparatus according to claim 1, wherein:
the at least one processor is further configured to carry out
a first acceptable rate display data preparing process of preparing first acceptable rate display data for use in displaying a first acceptable rate for each of a plurality of the first predetermined periods, the first acceptable rate being a probability that a value of the measured first sand property data is within the first reference range and a value of the measured second sand property data is within the second reference range, and
a second acceptable rate display data preparing process of preparing second acceptable rate display data for use in displaying a second acceptable rate for each of a plurality of the second predetermined periods, the second acceptable rate being a probability that a value of the measured third sand property data is within the third reference range and a value of the measured fourth sand property data is within the fourth reference range; and the display section is configured to further display the first acceptable rate display data and the second acceptable rate display data in the display area in which the first graph and the second graph are displayed.

4. The display apparatus according to claim 1, wherein:
the at least one processor is configured to further carry out
a first unacceptable rate display data preparing process of preparing first unacceptable rate display data for use in displaying a first unacceptable rate for each of a plurality of the first predetermined periods, the first unacceptable rate being a probability that a value of the measured first sand property data is outside the first reference range or a value of the measured second sand property data is outside the second reference range, and
a second unacceptable rate display data preparing process of preparing second unacceptable rate display data for use in displaying a second unacceptable rate for each of a plurality of the second predetermined periods, the second unacceptable rate being a probability that a value of the measured third sand property data is outside the third reference range or a value of the measured fourth sand property data is outside the fourth reference range; and wherein the display section is configured to further display the first unacceptable rate display data and the second unacceptable rate display data in the display area in which the first graph and the second graph are displayed.

5. The display apparatus according to claim 1, further comprising:
a first storage section configured to pre-store the first reference range and the second reference range therein; and
a second storage section configured to pre-store the third reference range and the fourth reference range therein.

6. The display apparatus according to claim 1, further comprising a storage section configured to pre-store the remedial measure assistance information therein.

* * * * *